United States Patent
Witham

(10) Patent No.: US 8,671,738 B2
(45) Date of Patent: Mar. 18, 2014

(54) CASCADE IMPACTOR

(76) Inventor: Clyde L. Witham, Saratoga Springs, UT (US)

( * ) Notice: Subject to any disclaimer, the term of this patent is extended or adjusted under 35 U.S.C. 154(b) by 800 days.

(21) Appl. No.: 12/681,241

(22) PCT Filed: Sep. 26, 2008

(86) PCT No.: PCT/US2008/077769
§ 371 (c)(1),
(2), (4) Date: Jul. 17, 2010

(87) PCT Pub. No.: WO2009/045866
PCT Pub. Date: Apr. 9, 2009

(65) Prior Publication Data
US 2010/0288057 A1 Nov. 18, 2010

Related U.S. Application Data

(60) Provisional application No. 60/977,070, filed on Oct. 2, 2007.

(51) Int. Cl.
*G01N 1/22* (2006.01)

(52) U.S. Cl.
USPC .............. 73/28.05; 73/863.23; 73/863.22

(58) Field of Classification Search
USPC .................. 73/863.22–863.23, 28.05
See application file for complete search history.

(56) References Cited

U.S. PATENT DOCUMENTS

| | | | |
|---|---|---|---|
| 3,693,457 A | 9/1972 | Pilat | |
| 3,983,743 A | 10/1976 | Olin | |
| 4,290,384 A | 9/1981 | Ausschnitt | |
| 4,321,822 A | 3/1982 | Marple | |
| 4,327,594 A | 5/1982 | Nelson | |
| 4,354,862 A * | 10/1982 | Sgaslik | 55/296 |
| 4,640,140 A | 2/1987 | Burghoffer | |
| 4,930,359 A * | 6/1990 | Wolfrum et al. | 73/863.23 |
| 5,040,424 A * | 8/1991 | Marple et al. | 73/863.23 |
| 5,343,767 A | 9/1994 | Marple | |
| 5,681,752 A * | 10/1997 | Prather | 436/173 |
| 6,453,758 B1 | 9/2002 | Marple | |
| 6,723,568 B1 | 4/2004 | Liu | |
| 6,786,105 B1 | 9/2004 | Sioutas | |
| 2004/0250634 A1 | 12/2004 | Liu | |

OTHER PUBLICATIONS

Hickey, AJ, "Methods of Aerosol Particle Size Characterization", Chapter 8 in Hickey, AJ ed. Pharmaceutical Inhalation Aerosol Technology, Marcel Dekker, NY pp. 219-253.

(Continued)

*Primary Examiner* — Hezron E Williams
*Assistant Examiner* — Nashmiya Fayyaz

(57) ABSTRACT

The invention relates to low flow rate cascade impactors for sampling aerosols, notably but not limited to pharmaceutical aerosols. The impactor stages serve as both orifice plate and collecting cup, simplifying collection and analysis. The impactor is designed to operate at flow rates approximating the inspiratory flow rates of young children and infants. Also presented is a method of and apparatus for applying a coating material to the collection surface of the stages after an impactor is assembled for use. The method entails generation of a polydisperse aerosol and sampling into the impactor. The coating substance improves the trapping of particles on the stages. The apparatus and method of application limit the amount of coating material applied and confines it to the regions of particle impact opposite the stage orifices.

25 Claims, 8 Drawing Sheets

(56) References Cited

OTHER PUBLICATIONS

Marple, VA and Rubow, KL, "Theory and Guidelines", Chapter 4 in Lodge, JP and Chan, TL eds, Cascade Impactor, American Industrial Hygiene Association, 1986, pp. 79-101.

US Pharmacopeia Chapter 601, "Aerosols, Nasal Sprays, Metered-Dose Inhalers, and Dry Powder Inhalers".

Coates, AL, et al., "How Many Infective Viral Particles are Necessary for Successful Mass Measles Immunization by Aerosol", Vaccine 24:1578-1585,2006.

Marple, VA and Willeke,K, "Inertial impactors: theory, design, and use" in Liu BYH ed., Fine Particles, Aerosol Generation, Measurement, Sampling, and Analysis, Academic Press, NY, 1975 pp. 412-446.

Mugele, RA and Evans, HD, "Droplet Size Distribution in Sprays", Indust. and Engineering Chem. 43(6)1317-1324, 1951.

Marple, VA, "History of Impactors—The First 110 Years", Aerosol Science and Technol 38:247-292, 2004.

Moore, KF, et al., "Development of a multi-stage cloud water collector part 1: Design and field performance evaluation", Atmospheric Environment 36:31-44, 2002.

Nasr, MM, et al., "Effect of drug load and plate coating on the particle size distribution of a commercial albuterol metered dose inhaler (MDI) determined using the Andersen and Marple-Miller cascade impactors", Pharmaceutical Research 14:1437-1443, 1997.

\* cited by examiner

CASCADE IMPACTOR

CROSS-REFERENCE TO RELATED APPLICATIONS

This application claims the benefit of U.S. Provisional Application No. 60/977,070 filed 2 Oct. 2007, and PCT/U.S.08/77769 filed 26 Sep. 2008 which are incorporated herein by reference.

FIELD OF THE INVENTION

The present invention relates to the field of aerosol particle sampling. In particular, the invention relates to cascade impactors for sampling pharmaceutical aerosol preparations at low flow rates.

BACKGROUND OF THE INVENTION

A cascade impactor is an aerosol-sampling device that samples and separates the aerosol according to the aerodynamic properties of the particles. The typical cascade impactor has multiple collection stages arranged in series, with each collection stage having an orifice plate and a separate, removable collection surface positioned below the orifices (FIG. 1). With each successive stage, the total cross-sectional area of all of the orifices decreases in order to increase the velocity of the particle-laden air and thus the inertia of the entrained particles. The collection stages, or plates, serve as an impaction surface for the collection of the particles possessing inertia too great to be carried around the collection surface and onward to the next stage. Thus, successively smaller particles are collected on successive stages. The sizes of the particles collected on each stage, also referred to as the cut size, are primarily determined by the dimensions of the orifices above the stage and the volumetric flow rate through the impactor. Particles larger than the cut size are collected by inertial forces on the collection surface, while smaller ones remain entrained in the air stream to be collected on subsequent stages or a final collection filter. The cut size for a stage is the point of 50% collection efficiency.

Cascade impactors have been used in the pharmaceutical industry for many years (Hickey, A J. "Methods of Aerosol Particle Size Characterization" Chapter 8 in Hickey, A J ed. Pharmaceutical Inhalation Aerosol Technology, Marcel Dekker, NY 1992 pp. 219-253). The theory of operation is also known in the art (Marple, V A and Rubow, K L "Theory and Guidelines" Chapter 4 in Lodge, J P and Chan, T L eds. Cascade Impactor, Amer Indust Hygiene Assoc 1986 pp. 79-101). The pharmaceutical industry has long adapted cascade impactors designed for use in industrial and environmental sampling to characterize inhalers and devices for respiratory drug delivery (USP <601> Aerosols). These accepted pharmaceutical sampling devices are large in size and are typically operated at flow rates ranging from 28 to 100 liters per minute. At these high flow rates, numerous orifices must be used on each stage, resulting in operating conditions outside of the ideal range, and consequently non-ideal calibrations. Further, these devices have large collection surfaces requiring the collection of relatively large amounts of material to satisfy analytical method requirements. Their size also creates inaccuracies in measurement due to interstage losses of material unaccounted for in routine analysis (Marple V A, Willeke K. Inertial impactors: theory, design, and use. In: Fine Particles, Aerosol Generation, Measurement, Sampling, and Analysis. Liu BYH ed. Academic Press, NY, 1975). Further, these devices are not well suited for sampling aerosols intended for delivery to infants and children. Typical inhalation flow rates for children younger than 15 years of age range from 2 to 4 liters per minute (Coates, A. L., Tipples, G., Leung, K., Gray, M., Louca, E.; How Many Infective Viral Particles are Necessary for Successful Mass Measles Immunization by Aerosol; Vaccine; 24 (2006) 1578-1585). Infants, in particular, cannot be instructed to inhale at a rapid rate from an inhaler, and so must inhale at their normal tidal rate. Characterization of the dose and particle-size distribution from inhalation delivery devices operating at these low flow rates requires samplers, and in particular cascade impactors, operating at comparable flows.

Coating of Collection Surfaces with Adhesive Substances

To sample particles other than liquid droplets with a cascade impactor, it is generally accepted that a coating material must be placed on the collection stage. If not, the particles can bounce or be blown off or be re-entrained by the airflow, thus rendering the analysis of particle size erroneous. Typically the collection stages are coated by some means prior to sampling with a greasy, oily, or sticky substance, or a filter paper. Typically, the entire collection plate is coated by either dipping or spray or eyedropper application, and this can result in additional error for both gravimetric and quantitative chemical analysis, due to extraneous materials on the plate. Provided herein are embodiments of apparatuses and methods to apply coating material to only the small region opposite the orifices where the particles will impact, thus greatly reducing the quantity of extraneous materials required.

SUMMARY OF THE INVENTION

Compact, low flow rate impactors from which small quantities of pharmaceutical or other agents can be easily recovered are set forth in embodiments of the invention described herein.

Additional advantages of some embodiments of the invention include a reduced number of orifices compared to other cascade impactors, thus eliminating the inaccuracies due to many small holes. Another advantage of some embodiments includes the use of relatively large orifice diameters compared to currently available cascade impactors. The larger orifices allow for much easier removal of the particulate matter that may be lost in and around the orifices for analysis.

In certain embodiments, the invention comprises a cascade impactor with one or more concentrically nested stages.

In certain embodiments, the invention comprises concentric assembly of one or more impactor stages slidably coupled together to form a cascade impactor.

In certain embodiments of the invention, each impactor stage comprises a cylindrical cup further comprising an orifice-containing region and a particle collecting region.

In certain embodiments, the invention comprises one or more impactor stages wherein the orifices are located on the side walls of the stages.

In certain embodiments, the invention comprises one or more impactor stages wherein the collection surfaces are located on the side walls of the stages.

In certain embodiments, the invention comprises one or more impactor stages wherein the orifices are on the bottom surface of the stages.

In certain embodiments, the invention comprises one or more impactor stages wherein the collection surfaces are on the bottom surface of the stages.

In some embodiments of the invention the orifice containing region and the particle collecting regions are co-located.

In some embodiments of the invention, the orifice containing regions and the particle collecting regions are located on different surfaces of the impactor stages.

In some embodiments of the invention the particle collecting region is on the side wall of the stage while the orifice containing region is on the bottom surface of the stage.

In some embodiments of the invention the particle collecting region is on the bottom surface of the stage while the orifice containing region is on the side wall of the stage.

In certain embodiments, the invention comprises a cascade impactor designed to operate at between about 1 and about 10 liters per minute.

In certain embodiments, the invention comprises a cascade impactor designed to operate at between about 2 and about 8 liters per minute.

In certain embodiments, the invention comprises a cascade impactor designed to operate at between about 4 and about 6 liters per minute.

In certain embodiments, the invention comprises impactor stages designed to operate at between about 1 and about 10 liters per minute.

In certain embodiments, the invention comprises impactor stages designed to operate at between about 2 and about 8 liters per minute.

In certain embodiments, the invention comprises impactor stages designed to operate at between about 4 and about 6 liters per minute.

In certain embodiments, the invention comprises a cascade impactor for collection of particles suspended in air according to their aerodynamic properties.

In certain embodiments, the invention comprises one or more impactor stages for collection of particles suspended in air according to their aerodynamic properties.

In certain embodiments, the invention comprises a cascade impactor capable of collecting and separating aerosol particles having aerodynamic diameters between about 0.1 and about 15 micrometers.

In certain embodiments, the invention comprises a cascade impactor capable of collecting and separating aerosol particles having aerodynamic diameters between about 0.3 and about 12 micrometers.

In certain embodiments, the invention comprises a cascade impactor capable of collecting and separating aerosol particles having aerodynamic diameters between about 0.5 and about 8 micrometers.

In certain embodiments, the invention comprises impactor stages capable of collecting and separating aerosol particles having aerodynamic diameters between about 0.1 and about 15 micrometers.

In certain embodiments, the invention comprises impactor stages capable of collecting and separating aerosol particles having aerodynamic diameters between about 0.3 and about 12 micrometers.

In certain embodiments, the invention comprises impactor stages capable of collecting and separating aerosol particles having aerodynamic diameters between about 0.5 and about 8 micrometers.

In certain embodiments, the invention comprises impactor stages capable of collecting liquid aerosols in the bottom regions of stages that contain orifices and collection surfaces on the side walls.

In certain embodiments, the invention comprises a method of collecting liquid aerosols in the bottom regions of stages that contain orifices and collection surfaces on the side walls.

To improve the collection efficiency of cascade impactor stages and avoid bouncing of particles after impacting on the collecting surfaces, it is known that a coating material should be applied to the collection surfaces. Most methods involve spraying or dipping of collection plates (such as those shown schematically in FIG. 1) with a silicone or other coating material that will retain the particles on the surface following impaction. An apparatus and method described herein allows coating of the collection surfaces directly opposing the orifices after the impactor is assembled and ready for use. The method results in less coating material being applied and application only to the areas where it is needed. Using less coating material reduces the chances that it will interfere with the analytical methods for the pharmaceutical or test aerosol.

In certain embodiments, the invention comprises a method of applying a coating material to the collection surface of an impactor stage.

In certain embodiments, the invention comprises a method of applying a coating material simultaneously to the collection surfaces of all stages of a cascade impactor.

In certain embodiments, the invention comprises a method of applying a coating material to the collection surfaces of one or more impactor stages in the region directly opposing the orifices.

In certain embodiments of the invention, the coating material is selected from the group consisting of adhesives, greases, oils, silicone, Antifoam (Dow Corning, Midland Mich.,), glycerin, and phospholipids.

In certain embodiments, the invention comprises an apparatus for applying a coating material to the collection surfaces of a cascade impactor.

In certain embodiments, the invention comprises an apparatus for applying a coating material to the collection surfaces of a cascade impactor after it is assembled for use.

In certain embodiments of the invention, the coating material is selected from the group consisting of adhesives, greases, oils, silicone, Antifoam (Dow Corning, Midland Mich.), glycerin, and phospholipids.

In certain embodiments of the invention, the coating material is a silicone liquid.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 4 is a longitudinal view of the stage with one impactor stage mounted therein.

DETAILED DESCRIPTION OF THE INVENTION

Figure 1:
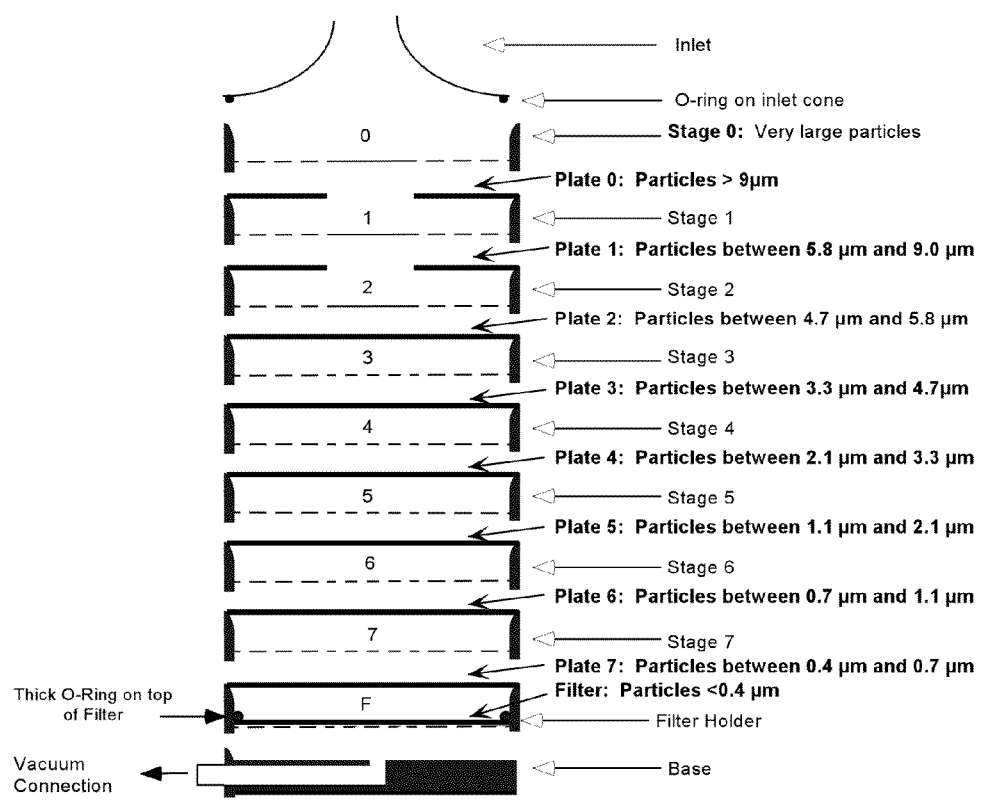
FIG. 1 is a cross-sectional schematic view of a typical cascade impactor used for pharmaceutical aerosol sampling.

The present invention provides embodiments for a novel cascade impactor. The stages of the impactor serve both as orifice plates and collection surfaces, thus minimizing the analytical requirements while simultaneously accounting for interstage particle losses. The orifices may be placed in the bottom surface of the collection stages, on the side walls of the collection stages, or a combination of both, depending upon the desired sampling flow rate. However, as discussed below, other configurations are also contemplated.

As used herein, the terms "comprising", "including", "such as", and "for example" are used in their open, non-limiting sense.

As used herein, the term "about" is used synonymously with "approximately." As such, values ranging between ±20% of the stated value may be considered equivalent for pressures and flow rates and ±30% for particle sizes.

As used herein, the term "aerosol" is defined as a suspension of solid particles or liquid droplets in air. Such a suspension is not required to be stable for any specific length of time, as it is recognized in the art that inhalation drug delivery devices (e.g., nebulizers, pressurized metered dose inhalers, dry powder inhalers, and the like) are capable of producing and emitting an extremely wide range of particle and droplet sizes.

As used herein, the terms atomizer and nebulizer are used interchangeably.

As used herein, the term "$D_{50}$" is defined as the median diameter. On an impactor stage 50% of the particles collected will be larger than the $D_{50}$ and 50% will be smaller. This is also referred to as the cutoff diameter for the stage.

As used herein, the terms "cutpoint", "cut size", and "cutoff diameter" refer to the median collection diameter for a given stage in the impactor.

As used herein, the term "Cunningham slip correction" refers to the correction to the particle diameter when it is close to the mean free path of the gas molecules. For particles greater than 1 micrometer, the correction is small, but becomes more significant below that size.

Calculation of the orifice diameters and corresponding flow rates to achieve desired cutoff diameters for the stages in an impactor may be accomplished using equations known in the art and presented by Marple and Willeke (Marple V A, Willeke K. Inertial impactors: theory, design, and use. In: *Fine Particles, Aerosol Generation, Measurement, Sampling, and Analysis*. Liu BYH ed. Academic Press, NY, 1975 pp 412-446) which is hereby incorporated by reference. Essentially, the cutoff diameter of 50% efficiency may be calculated from $$Stk_{50} = \frac{4\rho_p Q C D_{50}^2}{9\pi n \mu W^3}$$

where $\rho_p$ is the particle density (assumed to be 1 for measuring aerodynamic diameters), Q is the flow rate through the stage in cm$^3$/sec, C is the Cunningham slip correction, n is the number of orifices in the stage, $\mu$ is the viscosity of the sampled air (e.g., 1.81×10$^{-4}$ poise at normal temperature and pressure), W is the diameter, in cm, of a single orifice in the stage, and $Stk_{50}$ is the Stokes number at 50% collection efficiency.

This equation may be rearranged and solved for the product of the cutoff diameter times the square root of the Cunningham slip correction as follows:

$$\sqrt{C} D_{50} = \sqrt{\frac{9\pi \mu W^3}{4Q}} * \sqrt{Stk_{50}}$$

For round jets operating at Reynolds numbers greater than 100, $\sqrt{Stk_{50}}$ is approximately 0.47.

Turning now to the figures, FIG. 1 is a cross-sectional schematic view of a typical cascade impactor used for pharmaceutical aerosol sampling (Andersen Cascade Impactor, available from various manufacturers, e.g. Westech Instruments, Marietta, Ga.; Copley Scientific, Nottingham, UK; Thermo Fisher Scientific, Waltham, Mass.). Each stage has multiple orifices, ranging from 96 to 400 in number. The collection surfaces are separate metal plates that are separately inserted on supporting standoffs machined into each stage. O-rings seal each stage when the device is assembled and springs are used to compress the stages together to prevent air from leaking in between the stages during sampling.

Figure 2:
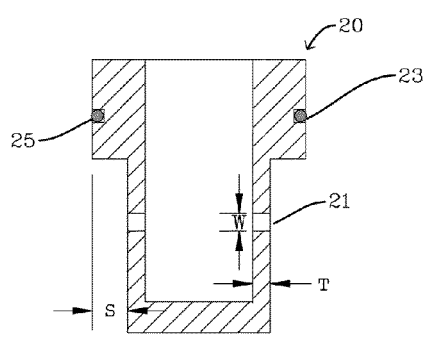
FIG. 2 is a cross-sectional view of an exemplary stage of one embodiment of the invention wherein the orifices are in the side wall of the impactor stage.

FIG. 2 depicts an exemplary impactor stage 20 of one embodiment of the invention. One or more holes 21 are drilled or molded within the side wall of the stage. These one or more holes comprise the orifices through which the particle-laden aerosol passes before being collected on a downstream collection surface. When more than one orifice is used, the orifices may be positioned equidistant around the circumference of the stage. The inner surface 24 of the stage comprises the collection surface for the preceding stage in an assembled cascade impactor. The collection surface for the stage shown in the figure is located on the next stage in the cascade. An O-ring 23 is positioned in a groove 25 to ensure a slidable air-tight seal of the stage with the next concentric stage in the cascade.

The stage can be machined from any metal material including stainless steel, aluminum, or brass. Alternatively, a variety of plastic materials may be used, including acetal resins (e.g., DELRIN, E. I. du Pont de Nemours and Company, Wilmington, Del.), or other solid polymeric materials (e.g., NYLON, TEFLON, E. I. du Pont de Nemours and Company, Wilmington, Del.).

In some embodiments, a combination of plastic and metal materials may be used.

Also shown in FIG. 2 are three design dimensions; the orifice diameter W, the spacing S between the orifice exit and the downstream collection surface, and the thickness T of the orifice. The diameter of the holes or orifices is referred to as W in the design equations presented above.

In some embodiments of the invention, the distance from the exit of the one or more orifices to the collection surface on the next stage (S) divided by the diameter of the orifice (W), S/W, is less than or equal to about 5.

In some embodiments, the ratio of the distances S/W is less than or equal to about 2.

In some embodiments, the ratio of the distances S/W is less than or equal to about 1.

In some embodiments, the ratio of the distances S/W is less than or equal to about 0.5.

In some embodiments the ratio of the distances S/W is greater than 1.

In still other embodiments, the ratio of the distances S/W is equal to 1.

In some embodiments, ratio of the distances S/W is between 0.5 and 5.

In some embodiments, the ratio of the distances S/W is equal to about 0.5, about 1, about 1.5, about 2.0, about 2.5, about 3.0, about 3.5, about 4.0, about 4.5, or about 5.0.

In some embodiments, the ratio of the thickness of the orifice to the diameter of the orifice (T/W) is equal to about 1.

In other embodiments T/W is greater than 1.

Figure 3:
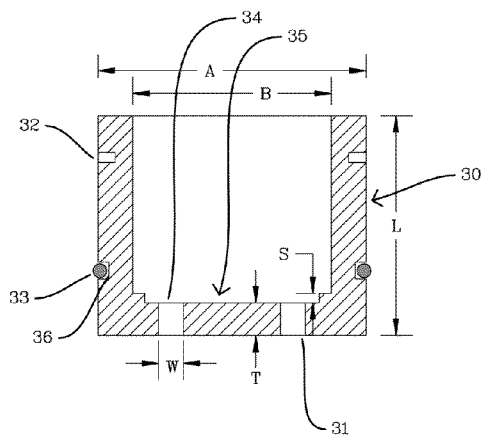
FIG. 3 is a cross-sectional view of an exemplary stage of one embodiment of the invention wherein the orifices are in the bottom of the collection stage.

FIG. 3 depicts an exemplary impactor stage 30 of one embodiment of the invention. One or more holes 31 are drilled or molded on the bottom surface of the stage. These holes comprise the one or more orifices through which the particle-laden aerosol passes before being collected on a downstream collection surface. The diameter of the holes is referred to as W in the design equations presented above. The inner surface 35 of the stage comprises the collection surface for the preceding stage. A raised portion 34 is machined or molded around the inside edge of the base of the stage to establish the desired distance (S) from the exit of the orifices on the preceding stage to the collection surface 35 on the illustrated stage. An O-ring 33 is positioned in a groove 36 to ensure a slidable air-tight seal of the stage with the next concentric stage in the cascade. Also shown in this figure are optional indentations 32 which are useful for assembly and disassembly of the impactor. Similar indentations may be incorporated, as needed on other embodiments and stages as presented and described herein.

In some embodiments of the invention, the distance from the exit of the one or more orifices to the collection surface on the next stage (S) divided by the diameter of the orifice (W), S/W, is less than or equal to about 5.

In some embodiments, the ratio of the distances S/W is less than or equal to about 2.

In some embodiments, the ratio of the distances S/W is less than or equal to about 1.

In some embodiments, the ratio of the distances S/W is less than or equal to about 0.5.

In some embodiments the ratio of the distances S/W is greater than 1.

In still other embodiments, the ratio of the distances S/W is equal to 1.

In some embodiments, ratio of the distances S/W is between 0.5 and 5.

In some embodiments, the ratio of the distances S/W is equal to about 0.5, about 1, about 1.5, about 2.0, about 2.5, about 3.0, about 3.5, about 4.0, about 4.5, or about 5.0.

In some embodiments, the ratio of the thickness of the orifice to the diameter of the orifice (T/W) is equal to about 1.

In other embodiments T/W is greater than 1.

The stage can be machined from any metal material including stainless steel, aluminum, or brass. Further, a variety of plastic materials may be used, including acetal resins (e.g., DELRIN, E. I. du Pont de Nemours and Company, Wilmington, Del.), or other solid polymeric materials (e.g., NYLON, TEFLON, E. I. du Pont de Nemours and Company, Wilmington, Del.).

In certain embodiments of the invention, a combination of metal and plastic materials may be used.

Figure 4:
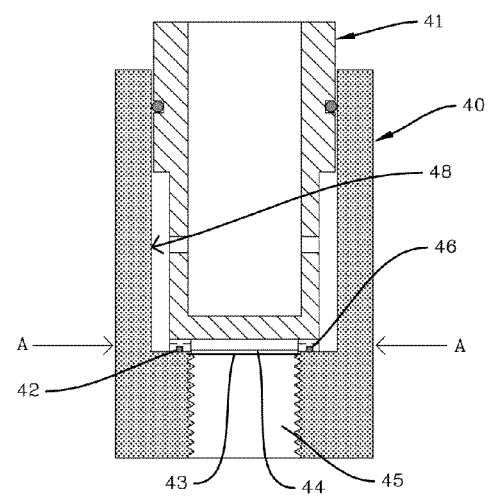
FIG. 4 shows cross-sectional views of a final filter stage for holding a filter within the impactor.
Figure 4A:
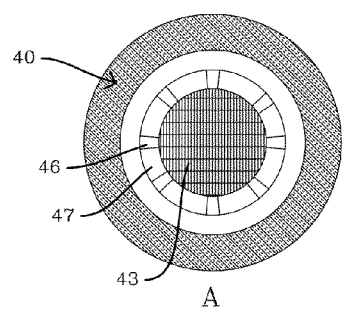
FIG. 4A is a transverse view through section A on FIG. 4.

FIG. 4 depicts a final filter stage 40 in which a filter 44 is mounted and retained by a pressure from the nested stage 41 above and or an O-ring 42. The filter is further supported by a mesh or screen 43. A vacuum source is connected with an optionally threaded fitting at 45. Also shown in FIG. 4 is the collection surface 48 for the aerosol impacted by the orifices in nested stage 41. FIG. 4A shows a transverse section through FIG. 4 at A. Protruding portions 46 of the preceding stage may be used to apply pressure to keep the O-ring 42 and filter 44 in place. Openings 47 allow air to flow from the preceding stage to the collection filter.

The stages can be machined from any metal material including stainless steel, aluminum, or brass. Further, a variety of plastic materials may be used, including acetal resins (e.g., DELRIN, E. I. du Pont de Nemours and Company, Wilmington, Del.), or other solid polymeric materials (e.g., NYLON, TEFLON, E. I. du Pont de Nemours and Company, Wilmington, Del.). In some embodiments, a combination of metal and plastic materials may be used.

Figure 5:
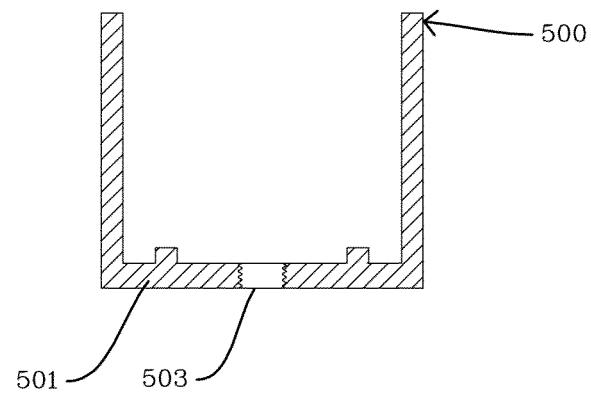
FIG. 5 is a cross-sectional view of a stage for connecting an external final filter.

FIG. 5 depicts a final stage 500 that allows connection of a cascade impactor as described herein to an external filter holder. An optional threaded connection 503 is located in the bottom, or in the side wall, where a vacuum source may be attached. One or more protrusions 501 support the preceding stage and ensure an airflow path to the collection filter.

The stage can be machined from any metal material including stainless steel, aluminum, or brass. Further, a variety of plastic materials may be used, including acetal resins (e.g., DELRIN, E. I. du Pont de Nemours and Company, Wilmington, Del.), or other solid polymeric materials (e.g., NYLON, TEFLON, E. I. du Pont de Nemours and Company, Wilmington, Del.). In some embodiments, a combination of metal and plastic may be used.

Figure 6:
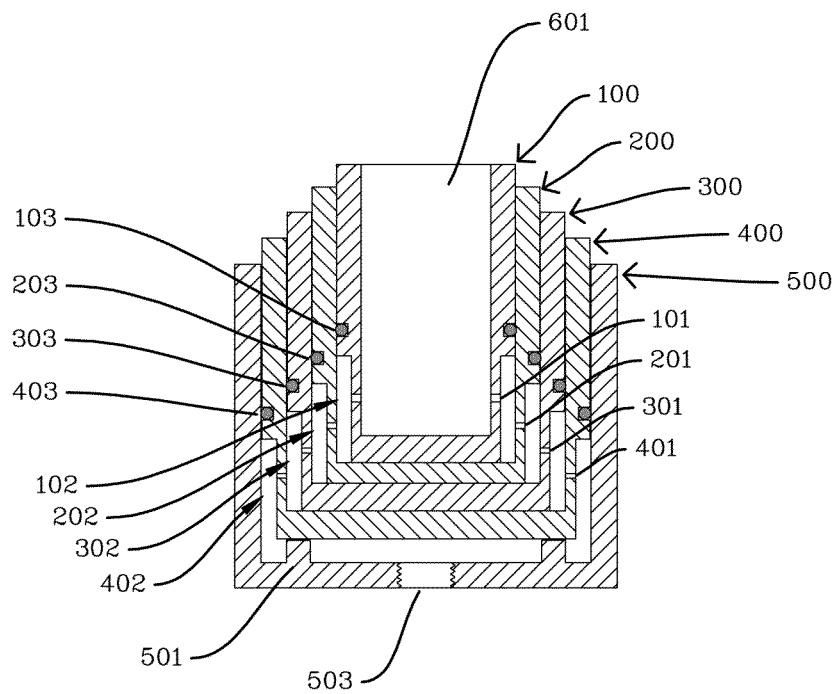
FIG. 6 is a cross-sectional view of an embodiment of the invention wherein the orifices are on the side walls of the collection stages.

FIG. 6 depicts a cross-sectional diagram of one embodiment of a fully assembled cascade impactor comprising 4 impaction stages and an external final filter stage. As shown, each stage is made to slidably seal with the next stage in the cascade by means of O-rings 103, 203, 303, and 403 situated in grooves machined or molded into the sides of the stages. After assembly, alternating stages may be rotated to establish an angle of between approximately 30 degrees to approximately 90 degrees, to assure that the orifices are not coplanar. In usage, an inhaler or other respiratory drug delivery device, for example, is connected to the inlet 601. Particle-laden air is pulled through the assembly by an external vacuum source connected at 503. As particle-laden air passes through the successive stages, 100, 200, 300, and 400, it carries the particles through each stage's orifices 101, 201, 301, and 401. Particles are impacted on their respective collection surfaces 102, 202, 302, and 402 downstream from the orifices as previously described according to their inertial properties. In this way, the aerosol particles are separated by aerodynamic diameter.

The stages can be machined from any metal material including stainless steel, aluminum, or brass. Further, a variety of plastic materials may be used, including acetal resins (e.g., DELRIN, E. I. du Pont de Nemours and Company, Wilmington, Del.), or other solid polymeric materials (e.g., NYLON, TEFLON, E. I. du Pont de Nemours and Company, Wilmington, Del.). In some embodiments, a combination of metal and plastic may be used.

Following collection of the sample, the impactor is disassembled and the amount of drug, or other characteristic of the particles, on each collection surface is assayed by an appropriate analytical method. The resulting particle size distribution or other descriptive parameters may be calculated from the analytical results.

If the impactor is used for environmental sampling, the inlet would remain open to the environment during sample collection and the stages would be assayed for the chemical or particle of interest.

The airflow rate through the assembled, operating cascade impactors is controlled externally with valves and or flow meters as is known in the art, and is determined from calculations of the stage parameters and the equations presented herein.

In some embodiments, the invention comprises cascade impactor comprising a series of one or more concentrically-arranged collection stages and a terminating filter or filter adapting stage, each collection stage comprising an elongated structure with a cylindrical shape, said elongated structure having a top end and a bottom end, the walls of said elongated structure having an inner surface and an outer surface and further characterized by a single inner diameter, a first outer diameter, and a second outer diameter, the top end being open and the bottom end being closed with a flat surface said elongated structure further comprising a region wherein the second outer diameter is less than the first outer diameter to form a orifice-containing region, the wall of said elongated structure further comprising at least one orifice positioned in said orifice-containing region and perpendicular to said wall and through which aerosol-containing air flows, the first outer diameter of said elongated structure being sized to fit within and slidably seal within the inner diameter of the next stage in the series.

In certain embodiments, the particles entrained in the sampled air are collected on the inner surface of the wall of the next stage in the series.

In some embodiments, orifices are placed equidistant around the circumference of the stage in the orifice-containing region.

In certain embodiments, the filter stage is further sized to receive the outer diameter of the last collection stage in said series.

In still other embodiments, the filter stage is connected externally from the series of stages.

In certain embodiments, the impactor is designed to operate at a flow rate between about 1 and about 15 lpm.

In certain embodiments, the impactor is designed to operate at a flow rate between about 1 and about 10 lpm.

In other embodiments, the impactor is designed to operate at a flow rate between about 2 and about 8 lpm.

In other embodiments, the impactor is designed to operate at a flow rate between about 4 and about 6 lpm.

In other embodiments, the impactor is designed to separate particles with sizes between about 0.1 and about 15 micrometers aerodynamic diameter.

In other embodiments, the impactor is designed to separate particles with sizes between about 0.3 and about 12 micrometers aerodynamic diameter.

In other embodiments, the impactor is designed to separate particles with sizes between about 0.5 and about 8 micrometers aerodynamic diameter.

In some embodiments of the invention, the distance from the exit of the one or more orifices to the collection surface on the next stage (S) divided by the diameter of the orifice (W), S/W, is less than or equal to about 5.

In some embodiments, the ratio of the distances S/W is less than or equal to about 2.

In some embodiments, the ratio of the distances S/W is less than or equal to about 1.

In some embodiments, the ratio of the distances S/W is less than or equal to about 0.5.

In some embodiments the ratio of the distances S/W is greater than 1.

In still other embodiments, the ratio of the distances S/W is equal to 1.

In some embodiments, ratio of the distances S/W is between 0.5 and 5.

In some embodiments, the ratio of the distances S/W is equal to about 0.5, about 1, about 1.5, about 2.0, about 2.5, about 3.0, about 3.5, about 4.0, about 4.5, or about 5.0.

In some embodiments, the ratio of the thickness of the orifice to the diameter of the orifice (T/W) is equal to about 1.

In other embodiments T/W is greater than 1.

Figure 7:
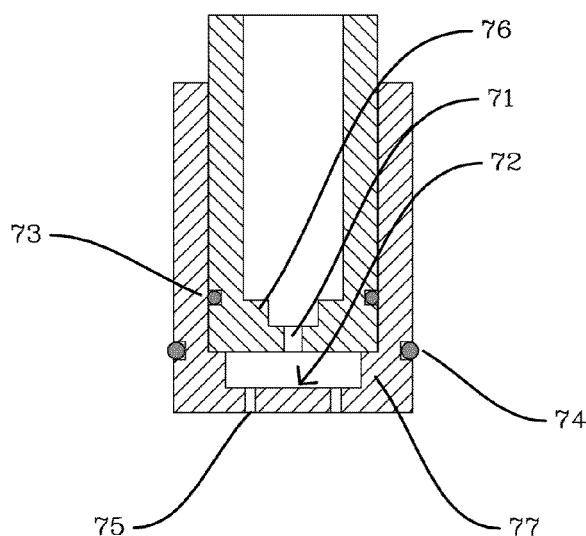
FIG. 7 is a cross-sectional view of an embodiment showing two assembled stages wherein the orifices are in the bottoms of the collection stages.

FIG. 7 shows two nested impactor stages wherein the orifices and collection surfaces are on the bottoms of the stages. Aerosol entering the first stage passes through that stage's orifice 71 and some of the particles impact on the collection surface 72. The remaining non-impacted aerosol continues through the orifices 75 in the next stage and onto a collection surface or filter as may be configured using the designs presented herein. O-rings 73 and 74 serve to slidably seal the stages and prevent leakage of air during sampling. A raised portion 76 and 77 is machined or molded into each stage to establish the desired spacing between the exit of the orifices and the collection surface.

Additional stages may be designed and constructed to assemble a cascade impactor covering a wide range of cutpoints according to the disclosure presented herein.

In some embodiments, the invention comprises a cascade impactor comprising a series of one or more concentrically-arranged collection stages and a terminating filter stage, each collection stage comprising an elongated structure with a cylindrical shape, said elongated structure having an open top end and a bottom end containing at least one orifice through which aerosol-containing air flows, the walls of said elongated structure having an inner surface and an outer surface and further characterized by a raised portion inside said bottom end, said raised portion sized to establish an orifice-to-collection surface distance, the outer diameter of said elongated structure being sized to fit within and slidably seal within the inner diameter of the next stage in the series.

In certain embodiments, the particles entrained in the sampled air are collected on the inner surface of the bottom end of the next stage in the series.

In some embodiments, filter stage is further sized to receive the outer diameter of the last collection stage in the series.

In some embodiments, the filter stage is connected externally from the series of stages.

In certain embodiments, the impactor is designed to operate at a flow rate between about 1 and about 15 lpm.

In certain embodiments, the impactor is designed to operate at a flow rate between about 1 and about 10 lpm.

In still other embodiments, the impactor is designed to operate at a flow rate between about 2 and about 8 lpm.

In still other embodiments, the impactor is designed to operate at a flow rate between about 4 and about 6 lpm.

In certain embodiments, the impactor is designed to separate particles with sizes between about 0.1 and about 15 micrometers aerodynamic diameter.

In still other embodiments, the impactor is designed to separate particles with sizes between about 0.3 and about 12 micrometers aerodynamic diameter.

In still other embodiments, the impactor is designed to separate particles with sizes between about 0.5 and about 8 micrometers aerodynamic diameter.

In some embodiments of the invention, the distance from the exit of the one or more orifices to the collection surface on the next stage (S) divided by the diameter of the orifice (W), S/W, is less than or equal to about 5.

In some embodiments, the ratio of the distances S/W is less than or equal to about 2.

In some embodiments, the ratio of the distances S/W is less than or equal to about 1.

In some embodiments, the ratio of the distances S/W is less than or equal to about 0.5.

In some embodiments the ratio of the distances S/W is greater than 1.

In still other embodiments, the ratio of the distances S/W is equal to 1.

In some embodiments, ratio of the distances S/W is between 0.5 and 5.

In some embodiments, the ratio of the distances S/W is equal to about 0.5, about 1, about 1.5, about 2.0, about 2.5, about 3.0, about 3.5, about 4.0, about 4.5, or about 5.0.

In some embodiments, the ratio of the thickness of the orifice to the diameter of the orifice (T/W) is equal to about 1.

In other embodiments T/W is greater than 1.

Figure 8:
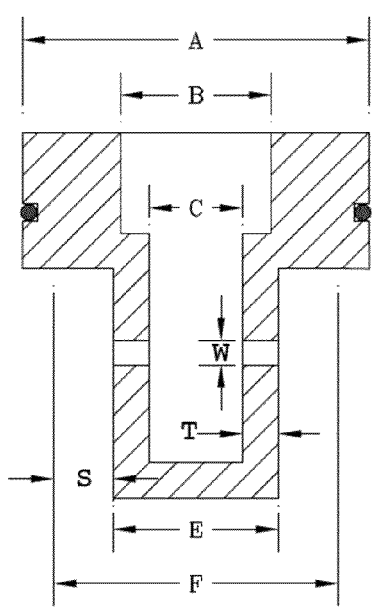
FIG. 8 is a cross-sectional view of an exemplary stage of one embodiment of the invention wherein the orifices are in the side wall of the collection stage with labels for dimensions referred to in some of the examples.

FIG. 8 is a cross-sectional view of an exemplary stage of an embodiment of the invention wherein the orifices are in the side wall of the collection stage. Shown in the figure are labels for dimensions referred to in some examples presented below.

In some embodiments of the invention, the distance from the exit of the one or more orifices to the collection surface on the next stage (S) divided by the diameter of the orifice (W), S/W, is less than or equal to about 5.

In some embodiments, the ratio of the distances S/W is less than or equal to about 2.

In some embodiments, the ratio of the distances S/W is less than or equal to about 1.

In some embodiments, the ratio of the distances S/W is less than or equal to about 0.5.

In some embodiments the ratio of the distances S/W is greater than 1.

In still other embodiments, the ratio of the distances S/W is equal to 1.

In some embodiments, ratio of the distances S/W is between 0.5 and 5.

In some embodiments, the ratio of the distances S/W is equal to about 0.5, about 1, about 1.5, about 2.0, about 2.5, about 3.0, about 3.5, about 4.0, about 4.5, or about 5.0.

In some embodiments, the ratio of the thickness of the orifice to the diameter of the orifice (T/W) is equal to about 1.

In other embodiments T/W is greater than 1.

In another aspect of the invention, a novel apparatus and method has been developed to apply a suitable coating to the collection surfaces of the stages of the impactor embodiments described herein, or to the collection surfaces of other impactors as are known in the art, in the region directly opposing the orifices of the stages. The coating is deposited exactly where the aerosol to be analyzed will be impacted and deposited. The method and apparatus provide for limiting application of extraneous coating to any other part of the impactor or collection substrates. The method and apparatus serve to form an aerosol of the coating material. Subsequent sampling of the coating aerosol through the cascade impactor under normal operating conditions ensures an ample and uniform coating.

It has been discovered that a very wide aerosol size distribution of coating-material droplets is required so that each impactor stage is uniformly coated. Such an aerosol can be generated by several atomization techniques, including rotary (e.g., spinning disc), hydraulic (e.g., liquid spray under pressure), pneumatic (e.g., twin fluid atomization), electrohydrodynamic, vibrating orifice, vibrating mesh, or other atomization techniques as are known in the art. An aerosol may also be produced by dissolution or suspension of the coating material in a suitable propellant (e.g., chlorofluorocarbon, hydrogen chlorofluorocarbon, hydrocarbon, nitrogen, carbon dioxide, etc.) and generating a spray from the resulting propellant pressure.

In some embodiments, the invention comprises a method of simultaneously coating the collection surfaces of an assembled cascade impactor comprising creating an aerosol comprising droplets of a liquid coating material, drawing said aerosol into the impactor with a vacuum source, and depositing said droplets of said coating material on the collection surfaces of the impactor stages.

Production of a broad size distribution often requires variation of some property that affects atomized droplet size In some embodiments of the invention, the method of coating the stages of the impactor comprises continually varying the viscosity of the coating material during the generation of the coating material aerosol.

In some embodiments of the invention, the method of coating the stages of the impactor comprises continually varying the density of the coating material during the generation of the coating material aerosol.

In still other embodiments of the invention, the method of coating the stages of the impactor comprises varying the input energy to the coating aerosol generator during the generation of the coating material.

The input energy to the coating aerosol generator may be varied in a number of ways depending upon the generator employed (e.g., rotational speed for a rotary atomizer, frequency of vibration for a vibrating orifice or vibrating mesh atomizer, temperature of the propellant for a propellant based atomizer, or pressure for a hydraulic or pneumatic atomizer).

In some embodiments of the invention the method of coating the impactor collection surfaces comprises varying the air pressure to a pneumatic nebulizer.

In some embodiments of the invention the method of coating the impactor collection surfaces comprises varying the air pressure to a disposable medical nebulizer.

In certain embodiments of the invention, the compressed air supply for the pneumatic nebulizer is stored in a rechargeable pressure container.

Figure 9:
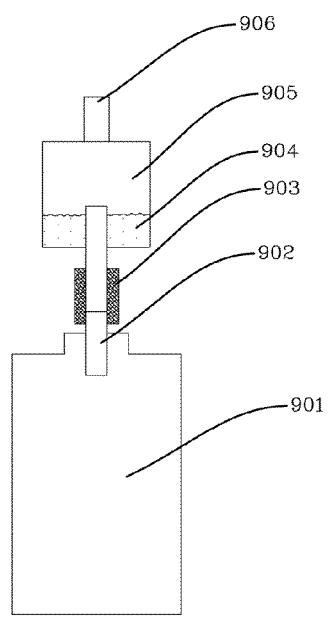
FIG. 9 is a schematic diagram of an apparatus for applying coating materials to the collection surfaces of an assembled cascade impactor.

FIG. 9 is a schematic diagram of an apparatus for applying coating materials to the collection surfaces of an assembled cascade impactor. A rechargeable, pressurized air container 901 with a valve 902 is connected via a coupling 903 to a compressed air nebulizer 905. The nebulizer is loaded with a quantity of liquid coating material 904. Upon opening the valve 902, the air pressure within the container is released through the nebulizer and an aerosol is produced at the outlet 906. Initially the aerosol is comprised of small droplets, but the sizes become larger as the pressure decreases with continual release of the air from the container.

Figure 10:
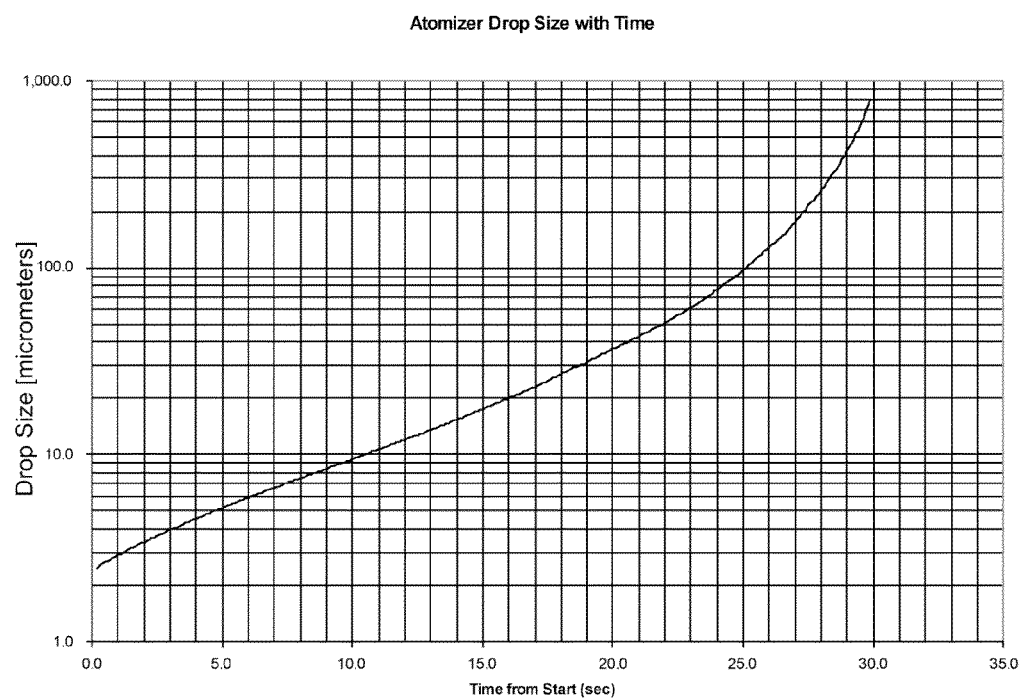
FIG. 10 is a graph of the particle size generated with time derived from the equations of Mugele (Mugele, R. A and HD Evans. Droplet Size Distribution in Sprays, Indust. and Engineering Chem. 43(6):1317-1324, 1951).

FIG. 10 shows a correlation of the particle size produced from the apparatus of FIG. 9 with time as the air pressure within the container is dissipated from about 145 psig to about 15 psig. This relationship was derived from the method of Mugele (Mugele, R. A and H D Evans. Droplet Size Distribution in Sprays, Indust. and Engineering Chem. 43(6):1317-1324, 1951; hereby incorporated by reference) using the characteristics of the nebulizer (jet-orifice diameter); the coating liquid viscosity, density, and surface tension; the gas viscosity; and the air pressure in the container. The relationship in FIG. 10 shows that the mean droplet diameter varies from about 2.5 to 18 micrometers when the coating apparatus of FIG. 9 is operated for about 15 seconds.

Air pressure is varied by charging a pressure container with compressed air, then exhausting the air supply from the pressurized container through the nebulizer. The volume of the container is selected to provide a sufficiently long operating time to aerosolize a given volume of coating material. Multiple actuations of the apparatus may used to aerosolize additional coating material. A broad size distribution of aerosol is produced as the pressure changes from high to low.

In some embodiments of the invention, the container of the apparatus is pressurized to a pressure up to approximately 10 times the recommended operating pressure of the nebulizer.

In other embodiments of the invention, the container of the apparatus is pressurized to a pressure up to approximately 5 times the recommended operating pressure of the nebulizer.

In still other embodiments of the invention, the container is pressurized to a pressure up to 2 times the recommended operating pressure of the nebulizer.

Figure 11:
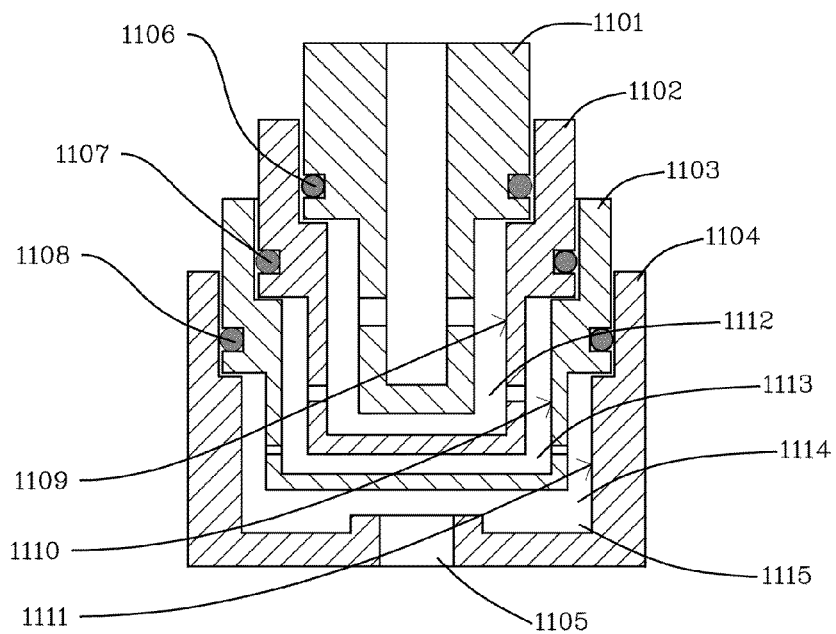
FIG. 11 is a cross-sectional view of another embodiment of the invention wherein the orifices are on the side walls of the collection stages.

Most commercial cascade impactors are not well suited for the collection of liquid droplet aerosols. This is because the collection surfaces are often horizontal plates and excess liquid remaining in regions of high velocity airflow can be re-entrained if excessive amounts are deposited. FIG. 11 shows an assembled embodiment of the invention utilizing the stage configuration of FIG. 8. This example embodiment has an inlet stage 1101, 3 collection stages 1102, 1103, and 1104 and an adapter 1105 for a final filter (not shown). O-rings 1106, 1107, and 1108 create slidable seals for assembling and disassembling the impactor. After assembly, the stages are rotated from an angle between approximately 30 degrees and approximately 90 degrees so that the orifices are offset from a common vertical plane. In operation with a liquid droplet aerosol, excess liquid may drip down the sides of the collection surfaces 1109, 1110, and 1111 to accumulate at the bottoms of the collection stages. In order to properly account for this collected material, this embodiment of the invention creates spaces 1112, 1113 and 1114 to accumulate the liquid at each stage without it being re-entrained by the high velocity airflow near the orifices. As shown in the figure, these spaces are created by resting the edge of one stage on the step-like portion of the next succeeding stage in the series. Further, the final stage contains an annular groove 1115 to prevent any accumulated liquid from passing onto the filter stage. This example embodiment allows for collection of significantly more liquid material than would be collectable on a horizontal flat surface, which in turn can help overcome low analytical detection limits. This embodiment is also well suited for use with dried aerosol particles.

The stages can be machined from any metal material including stainless steel, aluminum, or brass. Further, a variety of plastic materials may be used, including acetal resins (e.g., DELRIN, E. I. du Pont de Nemours and Company, Wilmington, Del.), or other solid polymeric materials (e.g., NYLON, TEFLON, E. I. du Pont de Nemours and Company, Wilmington, Del.). In some embodiments, a combination of metal and plastic may be used.

Additional stages may be designed and constructed to assemble a cascade impactor covering a wider range of cut-points according to the disclosure presented herein.

In some embodiments, the invention comprises a cascade impactor comprising a series of one or more concentrically-arranged collection stages and a terminating filter or filter adapter stage, each collection stage comprising an elongated structure with a cylindrical shape, said elongated structure having a top end and a bottom end, the walls of said elongated structure having an inner surface and an outer surface and further characterized by a first inner diameter, a second inner diameter, a first outer diameter and a second outer diameter, the top end of each stage being open and the bottom end being closed with a flat surface, said elongated structure further comprising a region wherein the second outer diameter is less than the first outer diameter to form a orifice-containing region, and a region wherein the first inner diameter is greater than the second inner diameter forming a step feature, the wall of said elongated structure further comprising one or more orifices positioned in said orifice-containing region and perpendicular to said wall and through which aerosol-containing air flows, the first outer diameter of said elongated structure being sized to fit within and slidably seal within the first inner diameter of the next stage and rest upon the step feature of said next stage in the series.

In certain embodiments with more than one orifice present, the orifices are spaced equidistant around the circumference of the stage wall.

In some embodiments, the first and second inner diameters are the same for the first stage.

In certain embodiments, the particles entrained in the sampled air are collected on the inner surface of the wall of the next stage in the series.

In some embodiments, the particles entrained in the sampled air are recovered from the bottom of the next stage in the series.

In certain embodiments, a filter stage is further sized to receive the first outer diameter of the last collection stage in said series.

In still other embodiments, a filter stage is connected externally from the series of stages.

In certain embodiments, the impactor is designed to operate at a flow rate between about 1 and about 15 lpm.

In certain embodiments, the impactor is designed to operate at a flow rate between about 1 and about 10 lpm.

In other embodiments, the impactor is designed to operate at a flow rate between about 2 and about 8 lpm.

In other embodiments, the impactor is designed to operate at a flow rate between about 4 and about 6 lpm.

In other embodiments, the impactor is designed to separate particles with sizes between about 0.1 and about 15 micrometers aerodynamic diameter.

In other embodiments, the impactor is designed to separate particles with sizes between about 0.3 and about 12 micrometers aerodynamic diameter.

In other embodiments, the impactor is designed to separate particles with sizes between about 0.5 and about 8 micrometers aerodynamic diameter.

EXAMPLES

The following examples are intended to be illustrative of various embodiments of the invention and are not intended to be limiting in nature.

Example 1

A cascade impactor with 4 collection stages and a filter stage was constructed according to the embodiment depicted in FIG. 3 and FIG. 7 and described in Table 1. This particular embodiment was designed to operate at 4 liters per minute total air flow. For the example described herein, clear plastic disks, 3.5 mil thick, were placed on each stage at the points of particle impaction in the cascade impactor to serve as particle collection substrates and allow for subsequent microscopic evaluation of the collected particles.

TABLE 1

Dimensions of one embodiment of a cascade impactor as described herein whereby one or more orifices are on the bottom surfaces of the impactor stages. The dimensions are referenced to FIG. 3.

| Stage | Dimensions [inches] | | | | | | No. Orifices | Cutoff Size $D_{50}(C)^{1/2}$ [micrometers] |
| | A | B | L | W | T | S | | |
| --- | --- | --- | --- | --- | --- | --- | --- | --- |
| 1 | 0.50 | 0.339 | 1.25 | 0.1850 | 0.1850 | — | 1 | 6.95 |
| 2 | 0.75 | 0.50 | 1.125 | 0.1130 | 0.1130 | 0.370 | 2 | 4.71 |
| 3 | 1.00 | 0.75 | 1.00 | 0.1130 | 0.1130 | 0.226 | 1 | 3.36 |
| 4 | 1.25 | 1.00 | 1.00 | 0.0390 | 0.0390 | 0.226 | 1 | 1.02 |
| Filter | 1.50 | 1.25 | 1.50 | — | — | 0.078 | — | <1.02 |

A = Nominal Outer Diameter [inches]
B = Nominal Inner Diameter [inches]
L = Length [inches]
W = Orifice Diameter [inches]
T = Orifice Length [inches]
S = Orifice to Collection Surface Spacing [inches]

Example 2

The apparatus of FIG. 9 was assembled. The container had a volume of about 475 ml and was pressurized to about 145 psig. A 1:100 dilution of silicone Antifoam (Dow Corning 1520) in water was added to a VixOne nebulizer (Westmed, Greenwood Village, Colo.). The valve was opened and an aerosol of the diluted silicone coating material was generated and sampled into the cascade impactor of Example 1 at a flow rate of 4 lpm. This method was repeated one more time, resulting in a total of 0.8 mg to 1.0 mg of coating material being deposited on the plastic disk collection surfaces of the impactor. The plastic disks described in Example 1 were removed and evaluated. The silicone was uniformly distributed (about 0.1 to 0.2 mg) on each collection substrate. Microscopic examination of the substrates indicated a much more uniform coating than when compared to conventional application by an eyedropper. The coating thickness was uniform and adequate for trapping particles, and the coated area opposing the orifices was about 1.5 to 2 times the diameter of the respective orifices for the stage.

Example 3

The impactor of Example 1 was once again reassembled, with clean clear plastic disks as described in Example 1. To coat the collection substrate surfaces, an aerosol of silicone Antifoam diluted 1:100 in water was produced by the apparatus depicted in FIG. 9 and the method described in Example 2. The Antifoam coating aerosol was sampled by the cascade impactor for 15 seconds with a flow rate of 4 l/min. Immediately following this, 5.1 mg of a test aerosol comprising a dry powder formulation of placebo measles vaccine was aerosolized into a spacer (Aerochamber Max, Trudell Medical, London, Ontario, Canada) and sampled into the impactor with a flow rate of 4 lpm for 30 seconds.

Example 4

After sampling the aerosol as described in Example 3, the plastic disks were removed and examined under the microscope to evaluate the size of particles collected on each stage. The results are shown in Table 2. The cut size for each stage was determined by measuring the diameters of the observed placebo vaccine aerosol particles collected on each individual substrate and estimating the median and range of the diameters. The data in Table 2 indicate that the cascade impactor separated the aerosol particles into size fractions as designed according to embodiments of the invention, with the cutoff diameter in the middle of the size range of particles collected.

TABLE 2

Microscopic Classification of the Particles Collected on the Stages and Determination of the Cut Sizes of the Stages of the Impactor Embodiment Described in Example 1.

| Stage | Smallest | Largest | Estimated Geometric Mean | Cut Point [micrometers] |
| --- | --- | --- | --- | --- |
| 1 | 1.5 | 14.4 | 7 | 6.95 |
| 2 | 1 | 6.4 | 5 | 4.71 |
| 3 | 1.3 | 4.5 | 3.5 | 3.36 |
| 4 | 0.7 | 2.8 | 1 | 1.02 |
| Filter | <1 | <1 | — | — |

Example 5

A cascade impactor with orifices and collection surfaces located on the side walls of the stages was constructed according to the parameters in Table 3 and single-stage embodiments shown in FIG. 2 and FIG. 8. Clear plastic disks were placed at the points of particle impaction to serve as particle collection surfaces. To coat the collection surfaces, an aerosol of Dow Antifoam diluted 1:100 in water was produced by the apparatus depicted in FIG. 9. The Antifoam coating aerosol was sampled by the cascade impactor for 15 seconds with a flow rate of 4 l/min. 5.1 mg of a placebo dry powder formulation of measles vaccine was aerosolized into a spacer (Aerochamber Max, Trudell Medical, London, Ontario, Canada) and sampled into the impactor with a flow rate of 4 l/min for 30 seconds.

TABLE 3

Dimensions of one embodiment of a cascade impactor as described herein whereby one or more orifices are on the side walls of the impactor stages. The dimensions are referenced to FIG. 8.

| Stage | Dimensions [inches] | | | | | | Orifice Diameter | No. Orifices | Cutoff Size $D_{50}(C)^{1/2}$ [micrometers] |
|---|---|---|---|---|---|---|---|---|---|
| | A | B | C | W | E | F | | | |
| 1 | 1.25 | — | 0.3390 | 0.1285 | 0.5960 | 1.1100 | 0.1285 | 3 | 6.96 |
| 2 | 1.75 | 1.25 | 1.1100 | 0.1015 | 1.3130 | 1.7190 | 0.1015 | 2 | 4.03 |
| 3 | 2.25 | 1.75 | 1.7190 | 0.0625 | 1.8440 | 2.0940 | 0.0625 | 2 | 1.99 |
| 4 | 2.50 | 2.25 | 2.0940 | 0.0390 | 2.1720 | 2.3280 | 0.0390 | 2 | 1.02 |
| 5 | 2.75 | 2.50 | 2.3280 | 0.0225 | 2.3730 | 2.4630 | 0.0210 | 4 | 0.66 |
| Filter | 3.00 | 2.75 | 2.4630 | — | 3 | 3 | — | — | <0.66 |

A = Nominal outer diameter [inches]
B = Nominal inner diameter [inches]
C = Inner diameter [inches]
W = Orifice diameter [inches]
E = Outer diameter [inches]
F = Second Inner Diameter of the Next Stage [inches]
The overall height of each stage in this example is approximately 1.50 inches.

Example 6

After collection, the clear disks were examined under a microscope. The resulting sizes of particles collected on each stage confirmed the calculated cutoff diameters for the stages and showed that the embodiment containing orifices in the side walls of the stages performs comparably to the embodiment in which the orifices are in the bottoms of the stages.

Example 7

An aerosol of ammonium fluorescein was produced in a wind tunnel by nebulizing a 5% ammonium fluorescein solution with an Aeroneb nebulizer (Nectar, San Carlos, Calif.) and allowed to dry to solid particles in the wind tunnel.

Ammonium fluorescein was chosen because of its widespread and long-known use in the art as a sensitive tracer material. It is very soluble in water, forms non-hygroscopic particles, and is easily analyzed with a spectrometer or a fluorometer down to a concentration of 1 nanogram per milliliter.

Figure 12:
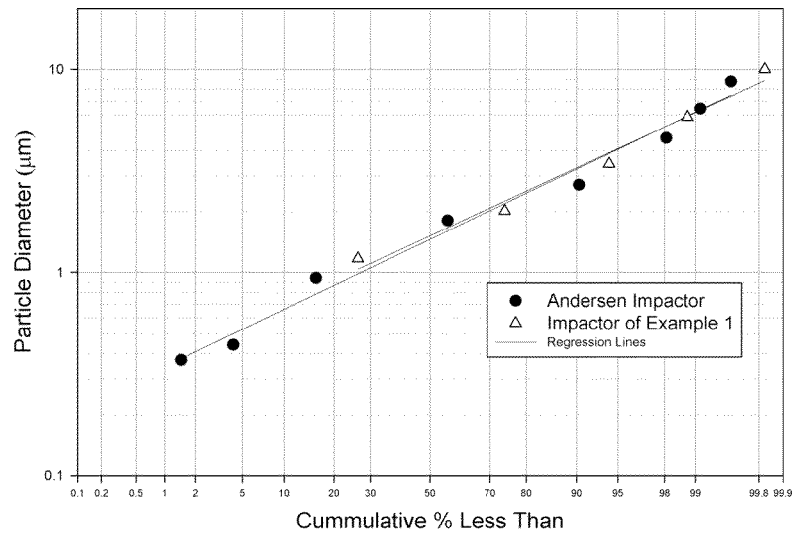
FIG. 12 is a graph of the size distributions for an aerosol sampled by both an Andersen cascade impactor and the embodiment described in Example 1.

The dried aerosol was sampled from the wind tunnel with the impactor of Example 1 and the mass of aerosol deposited on each stage was analyzed with a Turner Biosystems Picofluor fluorometer (Sunnyvale, Calif.). Clear plastic disks described in Example 1 were not used or needed for the collection of the fluorescein aerosol. An Andersen cascade impactor (Westech Instruments, Atlanta, Ga.) was also used to sample the aerosol from the wind tunnel and the mass collected on each stage was similarly analyzed. The size distributions as measured by both impactors were plotted and compared (FIG. 12), and indicated very good agreement between the two impactors.

Example 8

Figure 13:
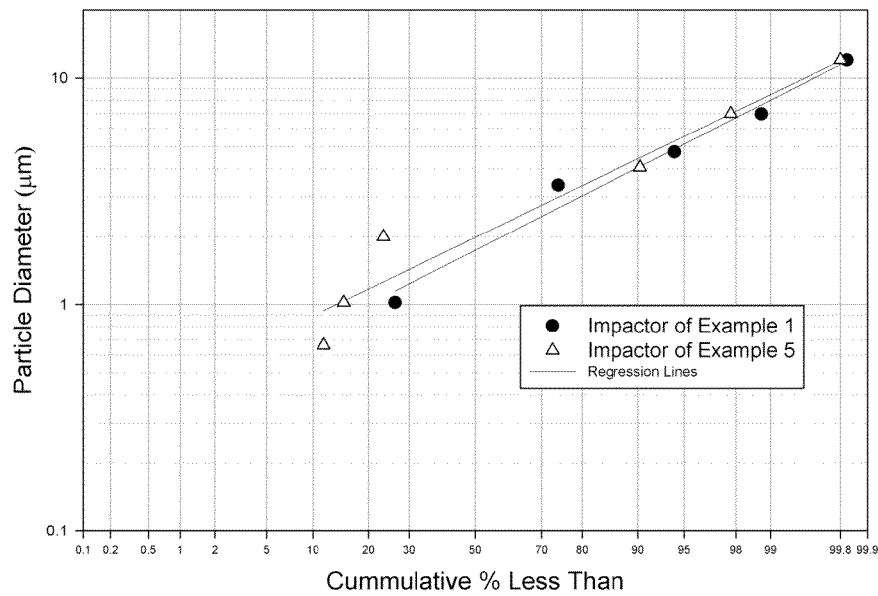
FIG. 13 is a graph comparing the size distribution of an aerosol measured by the embodiments described Example 1 and in Example 5.

A cascade impactor was constructed according to Example 5 and Table 3. An aerosol of ammonium fluorescein produced as described in Example 7 was sampled with the impactors of Examples 1 and 5. The resulting size distribution plot (FIG. 13) indicates good agreement between the two impactors.

Example 9

Figure 14:
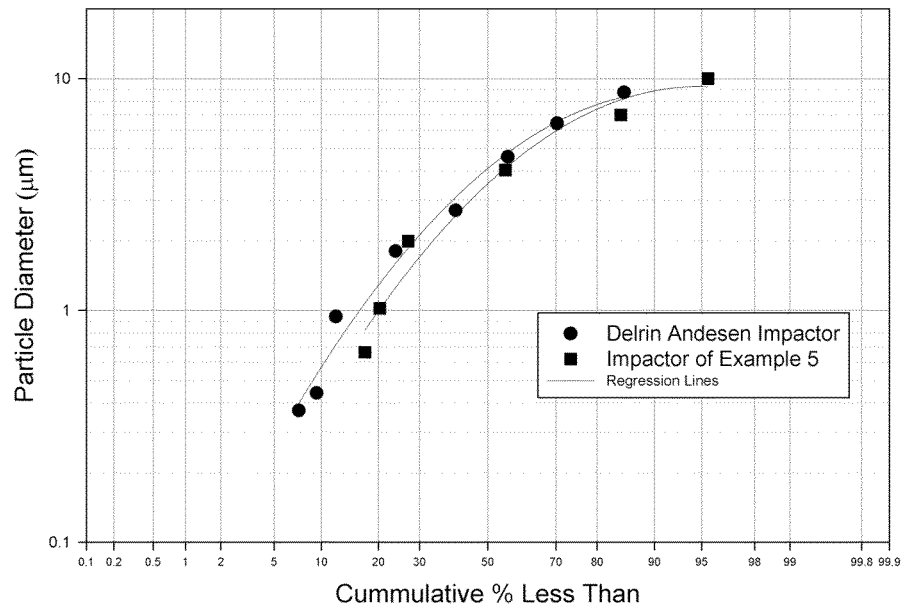
FIG. 14 is a graph comparing the size distribution of a liquid aerosol sampled by the embodiment described in Example 5 and a Delrin Andersen impactor.

A liquid aerosol of water and ammonium fluorescein is nebulized with a Bird Micronebulizer (Hudson RCI, Temecula Calif.). The impactor of Example 5 and a Delrin Andersen impactor (Westech Instruments, Atlanta, Ga.) specially designed for liquid aerosols are used to sample aerosol from the micronebulizer. The results are analyzed fluorometrically as in Example 7. A plot (FIG. 14) of the size distributions as measured by each of the impactors shows that the impactors are similar in the measured size distribution.

Example 10

Figure 15:
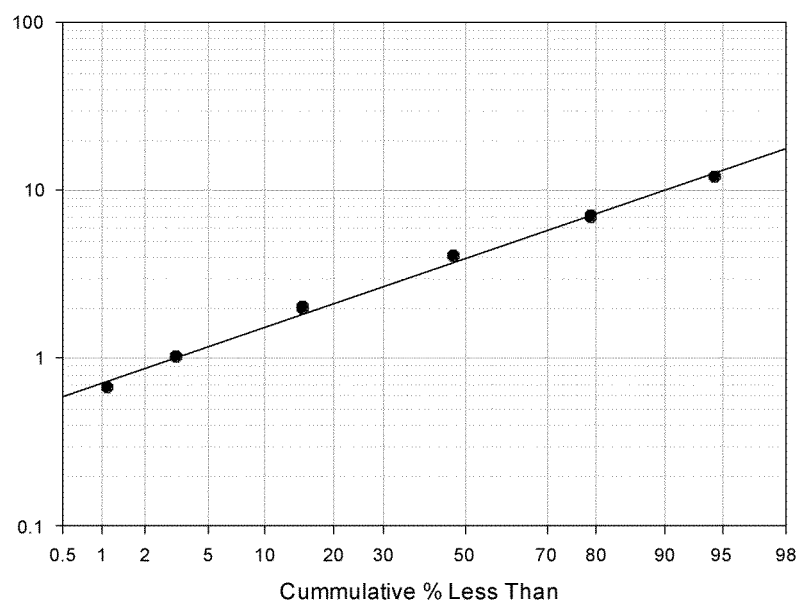
FIG. 15 is a graph of the size distribution of a coating aerosol produced according to Example 10.

The apparatus of Example 2 was assembled. A 1:10 dilution of silicon antifoam in water with 0.01% ammonium fluorescein added as a tracer was added to a VixOne nebulizer. The apparatus was pressurized to about 145 psi. The valve was opened and the aerosol produced was sampled into the impactor of Example 4 at 4 l/min. This method was repeated five more times, and then each of the impactor stages was analyzed fluorometrically. The size distribution is shown in FIG. 15. The mass median diameter of the grease aerosol was 3.92 micrometers, and the standard geometric deviation was 2.09. The amount of silicone grease deposited on each stage was calculated from analysis of the ammonium fluorescein tracer. Table 4 gives the approximate coverage under each impactor orifice. This aerosol was suitable for depositing a functional coating on each of the stages.

TABLE 4

Coverage of impactor stages with silicone grease

| Stage | Weight Grease (mg/sq. in.) |
|---|---|
| 1 | 20 |
| 2 | 98 |
| 3 | 260 |
| 4 | 250 |
| 5 | 69 |

Example 11

Figure 16:
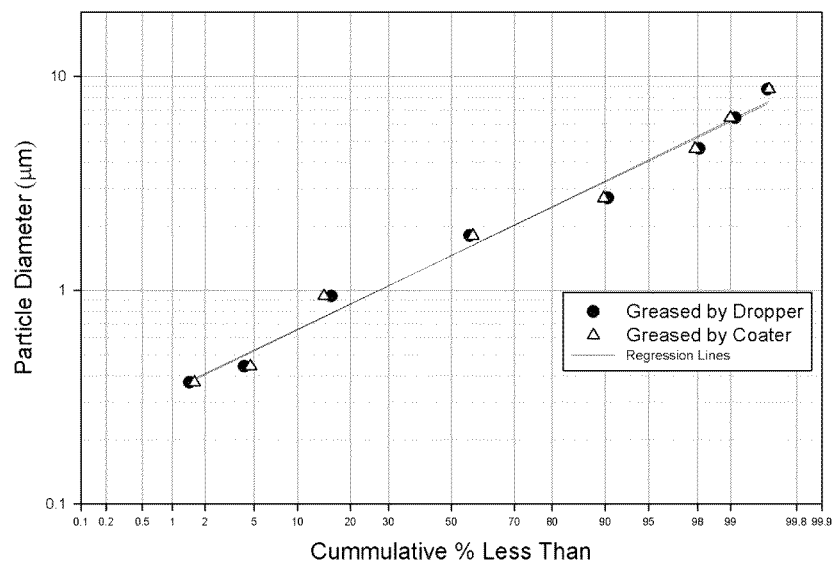
FIG. 16 is a graph comparing the size distributions of an aerosol produced and collected according to Example 11.

The apparatus of Example 2 was assembled. A 1:10 dilution of silicon antifoam in water was added to a VixOne nebulizer. The device was pressurized to about 145 psi. The valve was opened and the aerosol produced was sampled into an Andersen Cascade impactor at a flow rate of 28.3 l/min. The silicon anti-foam was allowed to dry by sampling clean, 31% relative humidity air for 12 minutes. The Andersen was then used to sample ammonium fluorescein test aerosol produced as described in Example 7. The plates were analyzed, and a size distribution of the aerosol was plotted. The same ammonium fluorescein aerosol method was used to sample into the Andersen impactor where the collection plates had been coated with grease in the traditional manner, using a dropper to cover each plate with grease, and allowing them to dry overnight. The size distribution plot (FIG. 16) indicates that the two methods of coating the plates with grease produce nearly identical sampling results for the test aerosol. Further, the aerosol method was suitable for depositing a functional coating on each of the stages.

While preferred embodiments of the invention have been shown and described herein, it will be obvious to those skilled in the art that such embodiments are provided by way of example only. Numerous variations, changes, and substitutions will now occur to those skilled in the art without departing from the invention. Specific dimensions given in the above examples are for the purposes of enablement of the examples. It should be understood that various alternatives to the embodiments of the invention described herein may be employed in practicing the invention, including alterations of the above stated specific dimensions. While the examples presented have a specific number of stages, it will be clear to one skilled in the art that additional collection stages may be similarly designed and added according to the teachings herein. It is intended that the following claims define the scope of the invention and that methods and structures within the scope of these claims and their equivalents be covered thereby.

What is claimed is:

1. A cascade impactor comprising:
a series of concentrically-arranged collection stages and a terminating filter or filter adapter stage,
each of said collection stages comprising an elongated structure with a cylindrical shape,
each of said elongated structures having a top end and a bottom end, the wall of each of said elongated structures having an inner surface and an outer surface and further characterized by a single inner diameter, a first outer diameter, and a second outer diameter,
the top end of each of said elongated structures being open and the bottom end of each of said elongated structures being closed with a flat surface,
each of said elongated structures further comprising a region wherein the second outer diameter is less than the first outer diameter to form an orifice-containing region on each of said elongated structures,
the wall of each of said elongated structures further comprising at least one orifice positioned in each of said orifice-containing regions and perpendicular to each of said walls and through which aerosol-containing air flows,
wherein, for each of said elongated structures, the first outer diameter is sized to fit within and slidably seal within the inner diameter of the elongated structure of the next stage in the series,
and wherein particles entrained in sampled air are collected on the inner surface of the wall of the stage opposite said respective at least one orifice.

2. The cascade impactor of claim 1 wherein said filter stage is further sized to receive the first outer diameter of the last collection stage in said series.

3. The cascade impactor of claim 1 wherein said filter stage is connected externally from the series of stages.

4. The cascade impactor of claim 1 designed to operate at a flow rate between about 1 and about 15 lpm.

5. The cascade impactor of claim 1 designed to operate at a flow rate between about 1 and about 10 lpm.

6. The cascade impactor of claim 1 designed to operate at a flow rate between about 2 and about 8 lpm.

7. The cascade impactor of claim 1 designed to operate at a flow rate between about 4 and about 6 lpm.

8. The cascade impactor of claim 1 designed to separate particles with sizes between about 0.1 and about 15 micrometers aerodynamic diameter.

9. The cascade impactor of claim 1 designed to separate particles with sizes between about 0.3 and about 12 micrometers aerodynamic diameter.

10. The cascade impactor of claim 1 designed to separate particles with sizes between about 0.5 and about 8 micrometers aerodynamic diameter.

11. A cascade impactor comprising a series of concentrically-arranged collection stages and a terminating filter or filter adapter stage,
each of said collection stages comprising an elongated structure with a cylindrical shape,
each of said elongated structures having a top end and a bottom end,
the wall of each of said elongated structures having an inner surface and an outer surface and further characterized by a first inner diameter, a second inner diameter, a first outer diameter and a second outer diameter,
the top end of each of said stages being open and the bottom end being closed with a flat surface,
each of said elongated structures further comprising a region wherein the second outer diameter is less than the first outer diameter to form an orifice-containing region, and a region wherein the first inner diameter is greater than the second inner diameter forming a step feature,
the wall of each of said elongated structures further comprising one or more orifices positioned in said orifice-containing regions of said elongated structures and perpendicular to said walls of said elongated structures and through which aerosol-containing air flows,
the first outer diameter of each of said elongated structures being sized to fit within and slidably seal within the first inner diameter of the elongated structure of the next stage and rest upon the step feature of said next stage in the series,
and wherein particles entrained in sampled air are collected on the inner surface of the wall of the stage opposite said respective one or more orifices.

12. The impactor of claim 11 wherein more than one orifice is present in one or more of said orifice-containing regions of said collection stages.

13. The impactor of claim 12 wherein said more than one orifices are spaced equidistant around the circumference of the walls of the collection stages.

14. The impactor of claim 11 wherein the first and second inner diameters are the same for the first stage.

15. The impactor of claim 11 wherein particles entrained in the sampled air are further recovered from the bottom of each collection stage in the series.

16. The impactor of claim 11 wherein said filter stage is further sized to receive the first outer diameter of the last collection stage in said series.

17. The impactor of claim 11 wherein said filter stage is connected externally from the series of collection stages.

18. The cascade impactor of claim 11 designed to operate at a flow rate between about 1 and about 15 lpm.

19. The cascade impactor of claim 11 designed to operate at a flow rate between about 1 and about 10 lpm.

20. The impactor of claim 11 designed to operate at a flow rate between about 2 and about 8 lpm.

21. The impactor of claim 11 designed to operate at a flow rate between about 4 and about 6 lpm.

22. The impactor of claim 11 designed to separate particles with sizes between about 0.1 and about 15 micrometers aerodynamic diameter.

23. The impactor of claim 11 designed to separate particles with sizes between about 0.3 and about 12 micrometers aerodynamic diameter.

24. The impactor of claim 11 designed to separate particles with sizes between about 0.5 and about 8 micrometers aerodynamic diameter.

25. The cascade impactor of claim 11 wherein excess liquid aerosol is collected in the bottom of each collection stage.

* * * * *